(12) United States Patent
Heath et al.

(10) Patent No.: US 8,393,899 B2
(45) Date of Patent: *Mar. 12, 2013

(54) ENDODONTIC INSTRUMENT AND METHOD (75) Inventors: Derek Heath, Vero Beach, FL (US); Steve Treadway, Johnson City, TN (US)

(73) Assignee: D&S Dental, LLC, Johnson City, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/361,284

(22) Filed: Jan. 30, 2012

(65) Prior Publication Data

US 2012/0196245 A1    Aug. 2, 2012

Related U.S. Application Data

(63) Continuation of application No. 12/397,961, filed on Mar. 4, 2009, now Pat. No. 8,105,085.

(60) Provisional application No. 61/033,675, filed on Mar. 4, 2008.

(51) Int. Cl.
*A61C 5/02* (2006.01)
(52) U.S. Cl. ........................................ 433/224; 433/102
(58) Field of Classification Search ................. 433/102, 433/165, 166, 224; 407/13, 16, 18, 19, 29.1; 29/896.1; 408/24, 25, 36, 118, 224, 225; 451/28, 48, 557, 61
See application file for complete search history.

(56) References Cited

U.S. PATENT DOCUMENTS

| | | | | | |
|---|---|---|---|---|---|
| 4,270,903 | A | * | 6/1981 | Nash | 433/165 |
| 5,026,284 | A | * | 6/1991 | Martin | 433/102 |
| 5,236,357 | A | * | 8/1993 | Randin | 433/102 |
| 5,857,852 | A | * | 1/1999 | Garman | 433/102 |

* cited by examiner

*Primary Examiner* — Todd Manahan
*Assistant Examiner* — Michael R Ballinger
(74) *Attorney, Agent, or Firm* — Luedeka Neely Group, PC (57) ABSTRACT

An endodontic instrument with an elongate shaft and a plurality of inverted frusto-conical sections with radial cutting edge disposed along a working portion of the shaft.

19 Claims, 6 Drawing Sheets

ENDODONTIC INSTRUMENT AND METHOD

CROSS REFERENCE TO RELATED APPLICATIONS

This application is a continuation of application Ser. No. 12/397,961 filed Mar. 4, 2009 now U.S. Pat. No. 8,105,085, which claims priority under 35 §119(e) to provisional application Ser. No. 61/033,675, filed Mar. 4, 2008, both of which are incorporated herein by reference.

BACKGROUND

In the field of endodontics, one of the most important and delicate procedures is that of cleaning or extirpating a diseased root canal to provide a properly dimensioned cavity while essentially maintaining the central axis of the canal for filling of the canal void and capping of the tooth. When done properly, this step enables substantially complete filling of the canal with biologically inert or restorative material without entrapping noxious tissue in the canal that could lead to failure of the therapy.

In a root canal procedure, the dentist removes diseased tissue and debris from the canal prior to filling the canal with a biologically inert or restorative filling material. In performing this procedure, the dentist must gain access to the entire canal, shaping it as appropriate. However, root canals often are very small in diameter, and they are sometimes quite curved. It is therefore often very difficult to gain access to the full length of the canal and to work all surfaces of the canal wall.

Many tools have been designed to perform the difficult task of cleaning and shaping root canals. Historically, dentists have used elongate, tapered endodontic files with helical cutting edges to remove the soft and hard material from within and adjacent the root canal area. These tools have generally been made by one of two basic processes. In one process, a file is created by twisting an elongate, tapered prismatic rod of either square or triangular cross section in order to create a file with one or more helical cutting/abrading edges ("K-file"). A second process involves grinding helical flutes into a circular or prismatic elongate, tapered rod to create a file with one or more helical cutting/abrading edges ("Hedstrom file").

Conventional endodontic instruments with helical cutting/abrading edges have certain endemic problems which, to some degree, have been tolerated and approached from a management perspective rather than an elimination perspective. For example, conventional endodontic instruments are made of metal alloys and are rotated within a root canal during use. Cutting surfaces on the instruments remove, chip, and/or abrade material from the root canal as the instrument is rotated and/or reciprocated roto-axially. This rotational movement creates torsional and other stresses in the instrument body, which can cause a portion of an instrument to break off in the root canal when the instrument becomes over-torqued and/or fatigued. Additionally, as the instrument is moved roto-axially in the canal, the instrument may begin to screw into the wall of the canal, especially in curved sections, rather than continuing down the canal towards the apical tip of the root. In some cases, this "screwing in" can cause the instrument to break through the side of the root canal and into surrounding tissue or bone. Or, it may begin to "drift" or displace laterally relative to the center axis of the canal as it is moved roto-axially.

These and other problems continue to plague practitioners and designers alike in their efforts to enlarge and prepare for filling the varied tooth root canal configurations in a manner substantially concentric with the natural or original canal curvature/shape to enable successful, effective, and permanent treatment therapies.

Accordingly, there is a need for improved endodontic instrument designs and methods that will avoid, minimize, or eliminate drawbacks and problems associated with conventional endodontic instruments including, but not limited to, "screwing in" issues and lateral displacements encountered during use of conventional endodontic instruments.

SUMMARY

The above and other needs are met by an endodontic instrument comprising an elongate stem and a plurality of inverted frusto-conical sections extending radially from the stem and arranged successively along the length of the stem, each projection including a circular shoulder or ledge and a tapered conical surface that tapers from an outer circular rim edge of the shoulder inwardly towards the centerline of the stem in a direction oriented from a promixal end of the stem to a distal end of the stem, whereby the instrument is capable of removing tissue from a root canal in a tooth using substantially only reciprocating movement substantially coaxial or parallel with the length axis of the canal.

In another embodiment, the invention includes a method for removing material from within or adjacent a root canal of a tooth using an elongate stem and a plurality of inverted frusto-conical projections extending radially from the stem and arranged successively along the length of the stem, each projection including a circular shoulder or ledge and a tapered conical surface that tapers from an outer circular rim edge of the shoulder inwardly towards the centerline of the stem in a direction oriented from a promixal end of the stem to a distal end of the stem, the method comprising the step of reciprocating the endodontic instrument in a direction substantially coaxial or parallel with the length axis of the canal, thereby removing undesirable tooth material.

One of the advantages of the present invention is that little or no torsional stress is placed on the endodontic instrument because the instrument accomplishes extirpation via axial reciprocating motion, rather than a traditional rotational motion. This lack of torsional stress significantly limits the likelihood that an instrument would break due to metal fatigue or torsion stress or strain—one of the most common reasons for endodontic instrument breakage. This is due to the fact that the tensile strength of the elongate instrument along its longitudinal axis is significantly greater than the torsional strength of the instrument.

Additionally, the lack of a twisting motion also minimizes the chances of endodontic instruments screwing into the wall of a root canal or drifting within the canal. In fact, the instrument substantially self-pilots itself down the root canal.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1A:
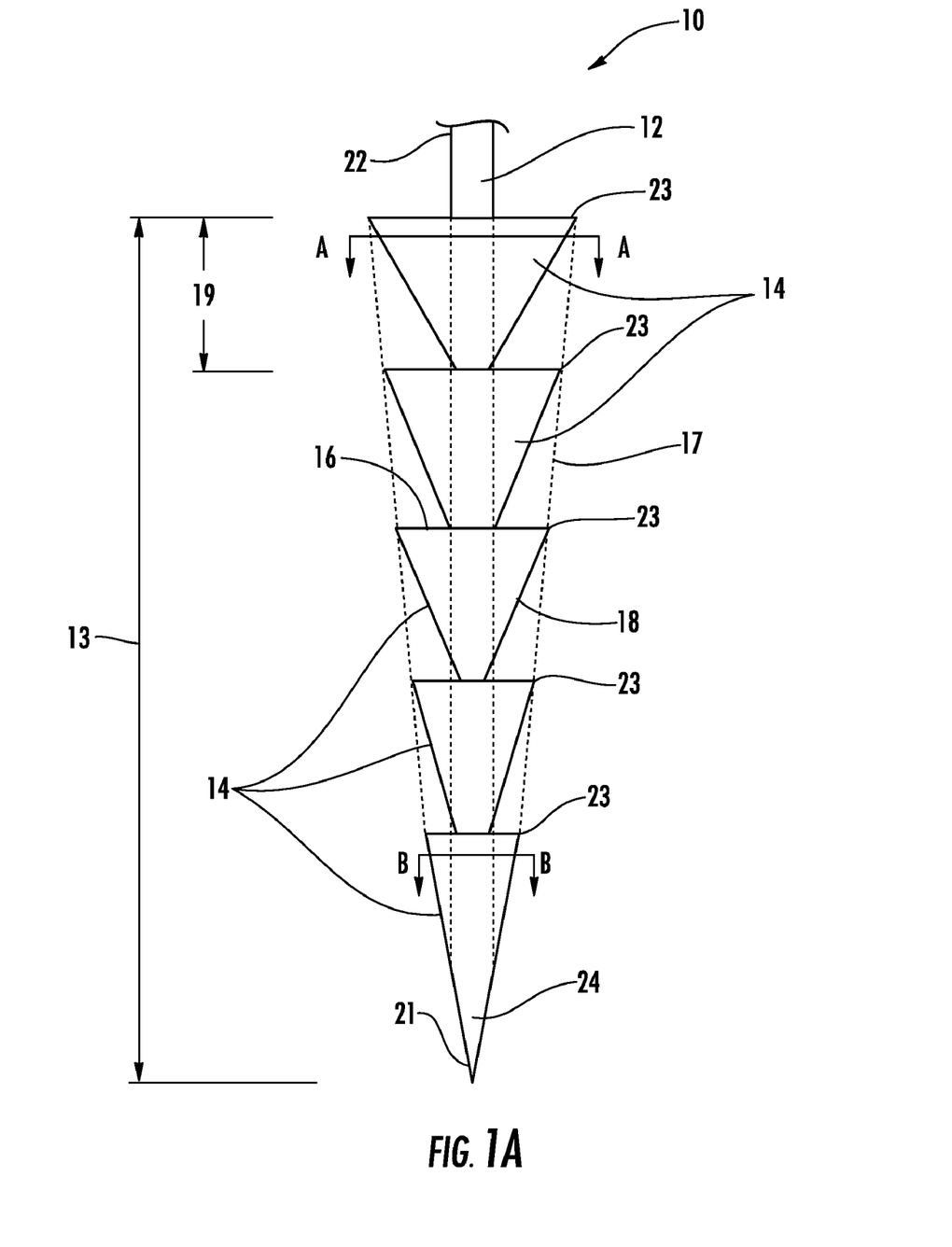
FIG. 1A shows an endodontic instrument according to an embodiment of the invention.

FIG. 1A illustrates features of an endodontic instrument 10 according to one preferred embodiment of the present invention. The elongate instrument is preferably formed from an elongate rod of stainless steel or nickel-titanium alloy having a diameter of from about 0.3 and to about 1.6 mm, although the rod may have a larger or smaller diameter and/or a varying diameter along its length as needed. In suitable embodiments, rods made from other suitable metals and/or alloys may be used. The elongate rod is preferably machined to form an elongate stem 12 and a plurality of projections or sections 14 integral with and extending from a working portion 13 adjacent the distal end of the stem. The length of the working portion preferably ranges from about 7 mm to about 20 mm, and is most preferably about 10 mm to about 16 mm. The proximal end of the instrument preferably includes a handle to facilitate hand manipulation of a file or a fitting portion for mating with the chuck of a dental handpiece.

Figure 1B:
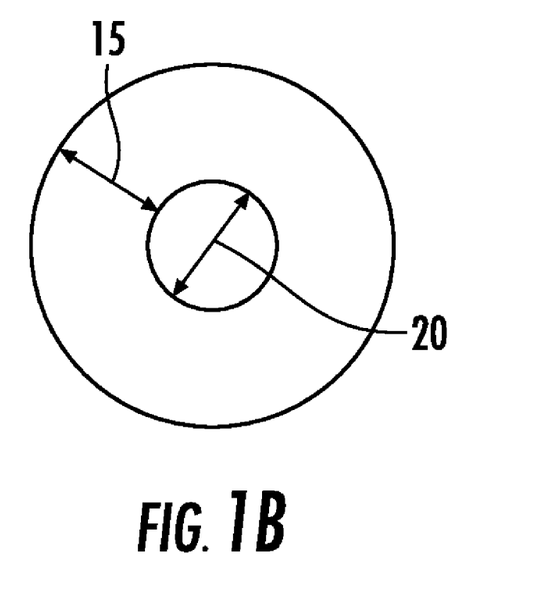
FIG. 1B shows a cross-sectional view of the endodontic instrument shown in FIG. 1A, as cut along line A-A, to illustrate the diameter of the stem and projection, which although drawn as separate features are preferably integral with each other.
Figure 1C:
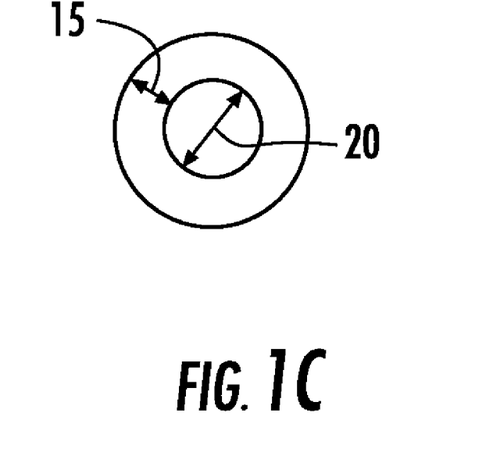
FIG. 1C shows a cross-sectional view of the endodontic instrument shown in FIG. 1A, as cut along line B-B to illustrate the diameter of the stem and projection, which although drawn as separate features are preferably integral with each other.

In the embodiment shown in FIG. 1A, the stem preferably includes a substantially uniform continuous cross-sectional diameter 20 from a proximal end of the working portion to a distal end of the working portion as shown in FIG. 1B, showing a cutaway at line A-A and FIG. 1C, showing a cutaway at line B-B. In a most preferred embodiment, the stem has a uniform cross-sectional diameter from a proximal end of the instrument adjacent the handle or handpiece fitting to the distal end of the instrument. The uniform cross sectional diameter of the stem at the core of the instrument provides the instrument with substantially uniform strength and flexibility along its length. This limits fatigue, which can build up and cause breakage in weaker, narrower portions of typical instruments with tapering cores. However, in alternate embodiments, a portion of the stem could have a positive or negative taper and/or different portions of the stem could have different taper rates.

The working portion 13 shown in FIG. 1A includes a limited number of projections for illustrative purposes. However, in various embodiments, the number of projections could be higher and preferably number from about 5 to about 30, although even more projections could be used in various embodiments of the invention. The plurality of projections are preferably substantially inverted frusto-conical in shape and extend circumferentially and outwardly along a working portion 13 of the stem, which typically extends from the distal end 24 of the instrument towards the proximal end. The projections are preferably continuous along the working portion with the apex area of frusto-conical projections adjacent the base area of successive projections. However, in some embodiments, there may be spacing between successive projections. Each of the projections 14 includes a radially extending ledge or shoulder 16 and a frusto-conical wall 18.

In a preferred embodiment, the projections taper toward the distal end of the instrument from the outside edge of the ledge to the outside diameter of the stem. The apex area of each of the projections is preferably substantially the same.

The ledge 16 of each projection may extend outwardly a uniform distance. However, in a preferred embodiment, the distance 15 from the outside diameter of the ledges to the stem decreases from the proximal end of the working portion to the distal end of the working portion such that the working diameter 17 of the instrument has a tapered configuration. In a preferred embodiment, the working diameter has a taper rate of from about 0.02 mm/mm to about 0.12 mm/mm. In certain embodiments, the frusto-conical wall 18 may extend from the outside edge of the ledge to the stem at substantially the same angle with respect to the center length axis C of the instrument. In an instrument with a tapered working diameter and a constant uniform diameter stem, a uniform angle of the frusto-conical walls results in projections having a decreasing axial length 19 from the proximal end to the distal end of the working portion. However, in other embodiments, each of the projections may have different taper rates and/or varying or uniform axial lengths.

Figure 3:
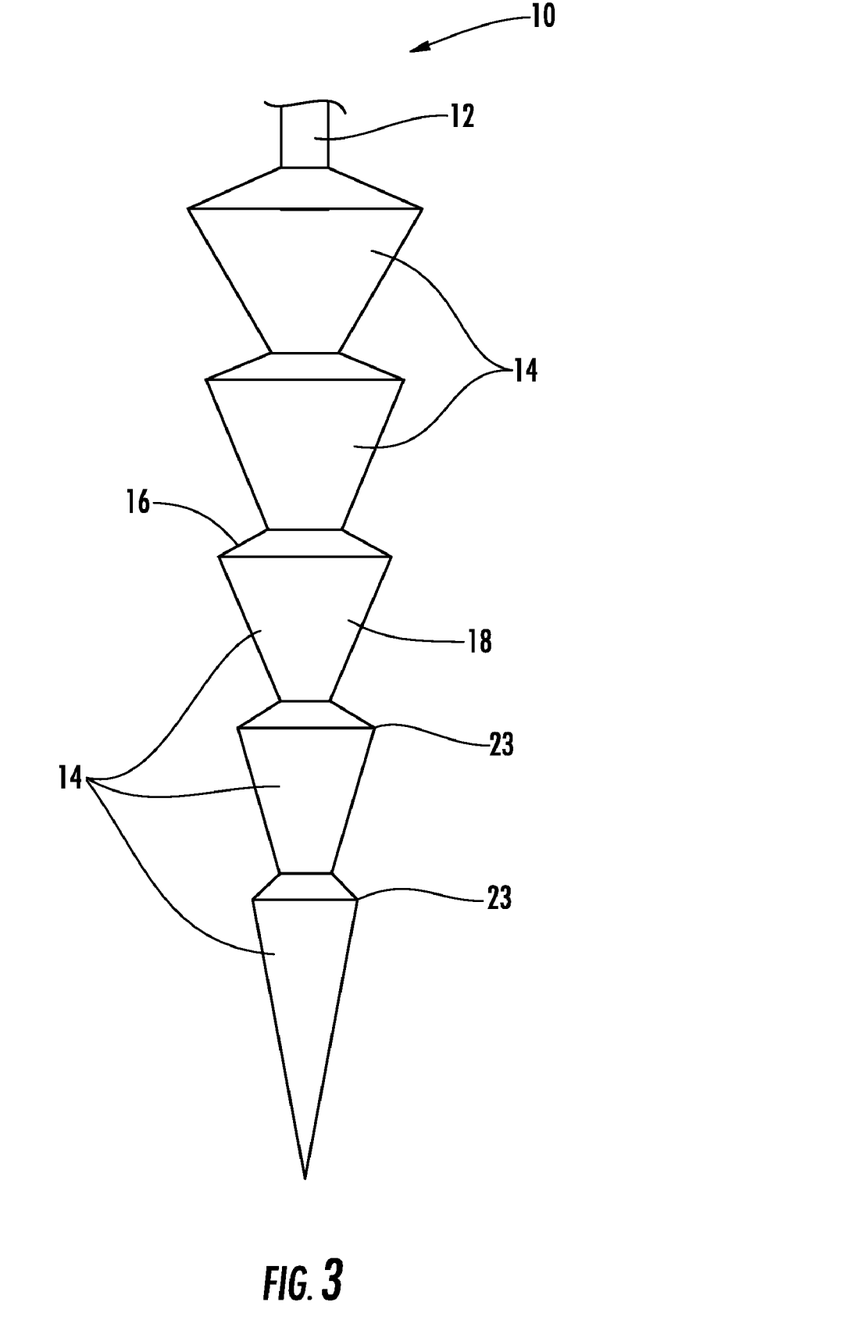
FIG. 3 shows a side view of an endodontic instrument with ledges oriented at a negative rake angle.
Figure 4:
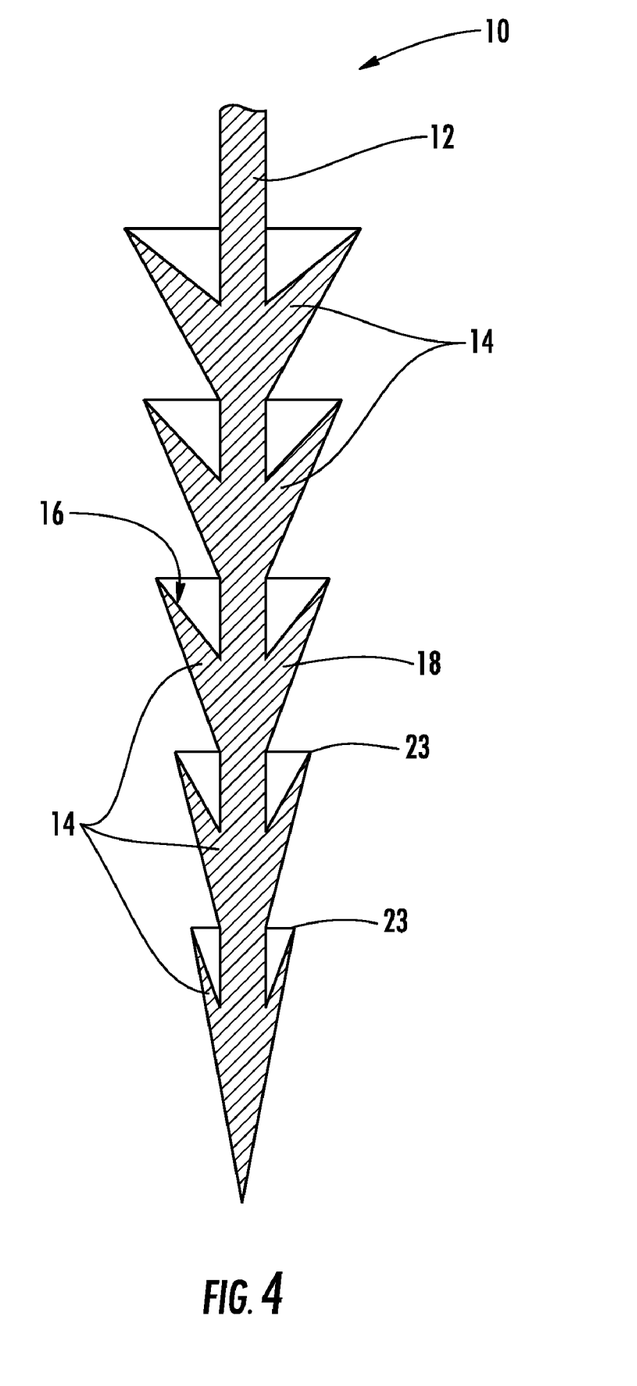
FIG. 4 shows a cutaway view of an endodontic instrument with ledges oriented at a positive rake angle.

The outside radial edge 23 of the ledge provides a cutting surface for removing tissue from the canal. The outside radial cutting edge 23 may be a substantially circular cutting edge extending continuously around the circumference of the instrument. However, in various embodiments, the radial cutting edge 23, ledge 16, and/or frusto-conical wall 18 may have discontinuous portions, with notches or openings formed in sections of their circumference. As the radial cutting edge cuts material from the root canal wall, removed debris 25 may accumulate on the ledge for removal from the canal when the instrument is removed from the canal. In certain embodiments, such as shown in FIG. 1, the ledge 16 extends radially outwardly from the stem to an edge substantially orthogonally at a substantially neutral rake angle, which maybe slightly positive or negative. In other embodiments, the ledges 16 are oriented at a negative rake angle such as shown in FIG. 3, or at a positive rake angle, such as shown in FIG. 4. Changing the cutting angle can provide a more or less aggressive cutting surface, as needed.

Figure 2:
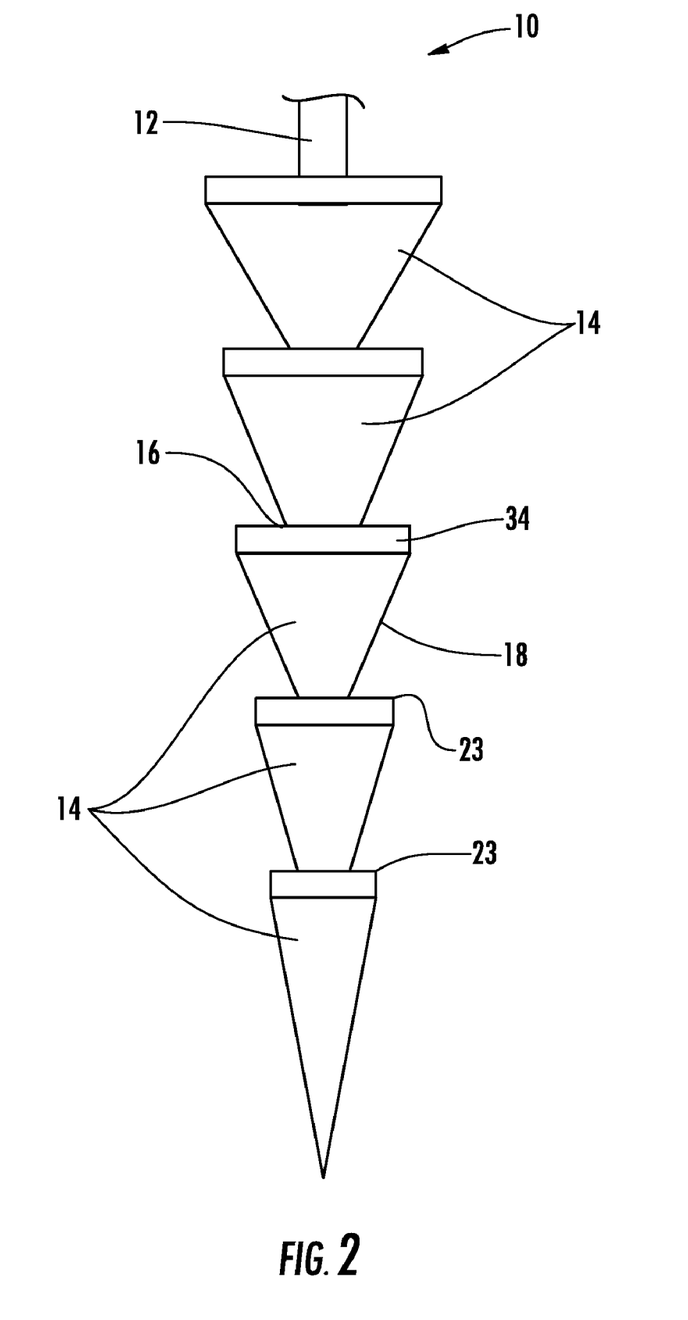
FIG. 2 shows a side view of an endodontic instrument with ledges, each ledge having a ledge layer.

In certain embodiments of the invention, the individual projections may have frusto-conical walls with portions disposed at different angles with respect to the center axis. For example, in the embodiment shown in FIG. 2 the frusto-conical wall 18 includes a portion substantially parallel with the center axis, thereby forming a radial land 34, and an angled portion. In other embodiments, the frusto-conical wall may have a first portion with a first angle that is greater or less than the angle of the remaining portion of the frusto-conical wall 18. Instruments with a frusto-conical wall 18 with a larger angle adjacent the radial cutting edge are believed to dig into the wall more aggressively when the instrument 10 is pushed into a root canal, whereas a frusto-conical wall with a smaller angle with respect to the length axis adjacent the radial cutting edge, such as a nontapered radial land, are believed to dig into the wall less aggressively when pushed into the canal.

In a preferred embodiment, unlike typical instruments with helical cutting surfaces, the outside radial cutting edges 23 of the ledges 16 provide substantially the only cutting surfaces for removal of tissue from a root canal. However, in certain embodiments of the invention, nonhelical cutting surfaces may be located on the periphery of the tapered surfaces of the projections or on other portions of the working portion of the stem to increase debriding of diseased tissue from the wall of the canal.

In various embodiments, the tip 21 of the endodontic instrument may have either a pointed or blunt configuration. In certain embodiments, the tip may be integral with the frusto-conical section adjacent the distal end of the instrument or the tip may be spaced from the frusto-conical section apex. Unlike typical endodontic instruments, according to preferred embodiments of the invention, the tip 21 of the instrument does not act as a cutting surface, which assists in limiting the "screwing in" effect when using the instrument of the present invention. However, in alternate embodiments, the tip 21 could include nonhelical cutting surfaces or other cutting surfaces known to those in the art to assist with root canal procedures.

Figure 5:
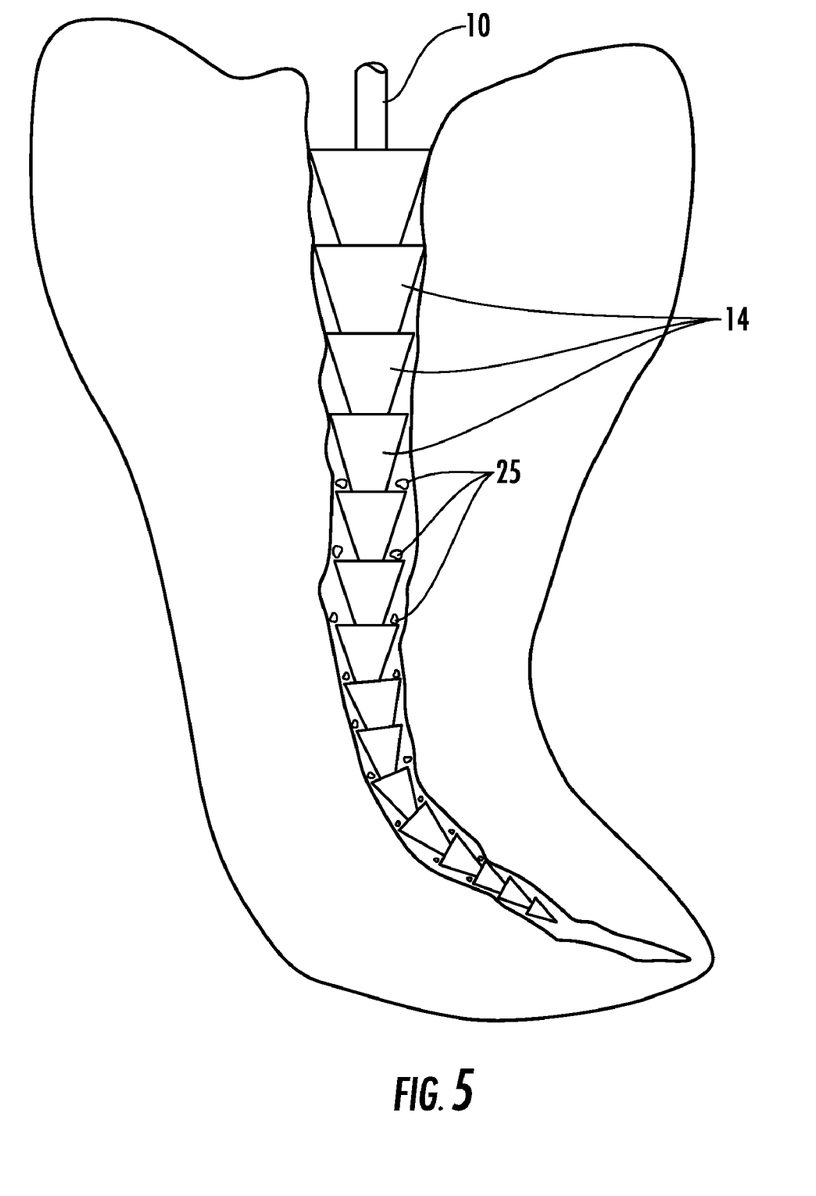
FIG. 5 is a graphical illustration of an embodiment of an endodontic instrument of the present invention inserted into a root canal of a tooth.

As indicated above, the instrument 10 includes a handle for hand-manipulation or is attachable to a handheld instrument which provides axial reciprocation. The instrument is inserted into a root canal of a tooth and an axial reciprocating motion is repeated within the canal coaxial with or parallel to the longitudinal axis of the root canal, thereby removing undesirable material from the tooth. During the reciprocating action, the instrument is pushed into the canal and digs into the tissue on the wall of the canal and then, as the instrument is pulled outward from the canal, the cutting surfaces 23 substantially shaves tissue or other material from the walls of the root canal, thereby removing diseased tissue and preparing the canal. As shown in FIG. 5, the removed material 25 accumulates on the ledges 16 of the projections 14 and is thereby removed from the canal when the instrument 10 is removed from the canal. The tapered, nonhelical configuration allows the instrument to substantially self-pilot itself through the canal, unlike typical helical instruments where the helical cutting surfaces tend to engage undesired portions of the root wall and screw in.

Additionally, in the preferred embodiment of the invention wherein the radial cutting edges 23 of the projections 14 provide the only cutting surfaces, the instruments 10 suffer little or no torsional stress because the instrument accomplishes extirpation via axial reciprocating motion, rather than a traditional rotational motion. This lack of torsional stress significantly limits the likelihood that an instrument will break due to metal fatigue or torsion stress or strain, one of the most common reasons for typical endodontic instrument breakage. The tensile strength of the elongate instrument along its longitudinal axis is significantly greater than the torsional strength of the instrument. Since the primary stresses in the instrument are tensile stresses, fatigue and breakage of the instrument 10 of the present invention are limited. Additionally, in the preferred embodiment of the instrument wherein the stem has a uniform diameter, the tensile strength of the instrument is substantially uniform along the length of the working portion, further limiting breakage due to tensile stress concentration which could occur at narrowed portions of an instrument. Accordingly, the instruments of the present invention minimizes the problems of instrument breakage faced by typical endodontic instruments with helical flutes and nonuniform diameter cores.

The foregoing description of preferred embodiments for this invention has been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An endodontic instrument adapted to be axially reciprocated within a root canal to remove material from walls of the root canal comprising an elongate shaft having a proximal end adjacent a handle adapted to be gripped by the hand of a user for being operated by hand or a fitting portion for connection to a dental handpiece for being mechanically operated by mechanism of the handpiece and a distal end terminating at a tip spaced from the proximal end by the length of the instrument, wherein the shaft includes a working portion adjacent the distal end which includes a plurality of inverted frusto-conical sections arranged adjacent one another along the length of working portion, each section having a ledge portion extending radially outwardly from a center length axis of the instrument to a radial cutting edge for engaging the walls of a canal and a first frusto-conical wall extending from the radial cutting edge towards the distal end of the instrument at a first angle with respect to the center length axis of the instrument, wherein successive radial cutting edges of at least a first portion of the working portion, moving towards the proximal end of the instrument, are disposed a greater distance from the center length axis than the radial cutting edge of the previous section so as to define an overall taper of the first portion of the working portion and wherein an apex diameter of each inverted frusto-conical section of the first portion of the working portion is the same.

2. The endodontic instrument of claim 1, wherein the overall taper of the first portion of the working portion is from 0.02 mm/mm to 0.12 mm/mm.

3. The endodontic instrument of claim 1, wherein the instrument is free of helical cutting surfaces such that the instrument does not screw in to the walls of the root canal during axial reciprocation and wherein the instrument is capable of removing material from a root canal wall in a tooth using only axial reciprocating motion within the root canal in a direction parallel with the length axis of the root canal.

4. The endodontic instrument of claim 1, wherein the shaft has a uniform cross sectional diameter from a proximal end to a distal end of the instrument.

5. The endodontic instrument of claim 1, wherein all successive radial cutting edges of the working portion moving from adjacent the distal end of the instrument towards the proximal end of the instrument are disposed a greater distance from the center length axis than the radial cutting edge of the previous section so as to define an overall taper of working portion and wherein an apex diameter of each inverted frusto-conical section of the working portion is the same.

6. The endodontic instrument of claim 1, wherein the radial cutting edges are circular cutting edges extending continuously about the circumference of the instrument.

7. The endodontic instrument of claim 1, wherein the radial cutting edges are discontinuous about the circumference of the instrument.

8. The endodontic instrument of claim 1, wherein the ledge portion extends orthogonally from the center length axis to the radial cutting edge to provide a cutting surface with a generally neutral rake angle.

9. The endodontic instrument of claim 1, wherein the ledge portion comprises a second frusto-conical wall disposed interiorly of the first frusto-conical wall, wherein the first and second frusto-conical walls converge to form the radial cutting edge.

10. The endodontic instrument of claim 1, wherein the ledge portion comprises a frusto-conical section disposed intermediate adjacent inverted frusto-conical sections and oriented in an opposite direction, wherein the frusto-conical section has a second frusto-conical wall which intersects the first frusto-conical wall of an adjacent inverted frusto-conical section.

11. The endodontic instrument of claim 1, wherein the first frusto-conical wall includes a first portion disposed at a first angle with respect to the center length axis of the instrument and a second portion disposed at a second angle with respect to the center length axis of the instrument that is different than the first angle.

12. The endodontic instrument of claim 1, wherein the axial length of at least a portion of the inverted frusto-conical sections is the same.

13. The endodontic instrument of claim 1, wherein the axial length of at least a portion of the inverted frusto-conical sections decreases from a proximal end of the working portion to a distal end of the working portion.

14. The endodontic instrument of claim 1, wherein the first frusto-conical walls of at least a portion of the frusto-conical sections are disposed at the same angle with respect to the center length axis of the instrument.

15. The endodontic instrument of claim 1, wherein the first frusto-conical walls of at least a portion of the frusto-conical sections are disposed at different angles with respect to the center length axis of the instrument.

16. The endodontic instrument of claim 1, wherein at least a portion of the plurality of sections are in a spaced apart relationship such that apexes of the first frusto-conical walls of the sections are not contiguous with adjacent sections.

17. The endodontic instruments of claim 1, wherein at least a portion of the plurality of sections are contiguous.

18. A method for removing material from a root canal of a tooth using an endodontic instrument comprising an elongate shaft having a proximal end adjacent a handle adapted to be gripped by the hand of a user for being operated by hand or a fitting portion for connection to a dental handpiece for being mechanically operated by mechanism of the handpiece and a distal end terminating in a tip spaced from the proximal end by the length of the instrument, wherein the shaft includes a working portion adjacent the distal end which includes a plurality of inverted frusto-conical sections arranged adjacent one another along the length of working portion, each section having a ledge portion extending radially outwardly from a center axis of the length of the instrument to a radial cutting edge for engaging the walls of a canal and a first frusto-conical wall extending from the radial cutting edge towards the distal end of the instrument at a first angle with respect to the center axis of the length of the instrument, the method comprising reciprocating the endodontic instrument in an axial direction parallel with the length axis of a root canal of a tooth to extirpate material from the walls of the root canal without rotational reciprocation, wherein successive radial cutting edges of at least a first portion of the working portion, moving towards the proximal end of the instrument, are disposed a greater distance from the center length axis than the radial cutting edge of the previous section so as to define an overall taper of the first portion of the working portion and wherein an apex diameter of each inverted frusto-conical section of the first portion of the working portion is the same.

19. The method of claim 18, wherein the instrument digs into the walls of a canal when pushed into the canal and substantially shaves material from the walls of the canal when the instrument is pulled from the canal.

* * * * *